(12) United States Patent
Pang et al.

(10) Patent No.: US 6,932,760 B1
(45) Date of Patent: Aug. 23, 2005

(54) AUTOCLAVABLE COUPLER FOR ENDOSCOPIC CAMERA SYSTEM

(75) Inventors: Chien Mien Pang, Milpitas, CA (US); YanPeng Ng, Santa Clara, CA (US); William H. L. Chang, Milpitas, CA (US)

(73) Assignee: Stryker Corporation, Kalamazoo, MI (US)

( * ) Notice: Subject to any disclaimer, the term of this patent is extended or adjusted under 35 U.S.C. 154(b) by 190 days.

(21) Appl. No.: 10/302,612

(22) Filed: Nov. 21, 2002

(51) Int. Cl.[7] .............................. A61B 1/04; A61B 1/12; H04N 7/18
(52) U.S. Cl. ........................... 600/112; 600/133; 348/73
(58) Field of Search ................ 600/112, 133, 167–169, 600/174; 359/823, 825–826; 348/73

(56) References Cited

U.S. PATENT DOCUMENTS

| | | | |
|---|---|---|---|
| 4,036,218 A * | 7/1977 | Yamashita et al. | 600/160 |
| 5,599,278 A * | 2/1997 | Hibbard | 600/133 |
| 5,836,867 A | 11/1998 | Speier et al. | |
| 5,868,665 A * | 2/1999 | Biggs | 600/112 |
| 6,019,719 A * | 2/2000 | Schulz et al. | 600/109 |
| 6,069,651 A * | 5/2000 | Tsuyuki et al. | 348/75 |
| 6,398,724 B1 * | 6/2002 | May et al. | 600/167 |
| 6,425,857 B1 * | 7/2002 | Rudischhauser et al. | 600/112 |
| 6,522,477 B2 * | 2/2003 | Anhalt | 600/112 |
| 6,537,208 B1 * | 3/2003 | Konno | 600/167 |
| 6,540,668 B1 * | 4/2003 | Schulz et al. | 600/112 |
| 6,767,322 B1 * | 7/2004 | Futatsugi et al. | 600/133 |
| 6,855,106 B2 * | 2/2005 | May et al. | 600/112 |
| 2001/0016679 A1 * | 8/2001 | Futatsugi et al. | 600/133 |
| 2002/0128539 A1 * | 9/2002 | Higuma et al. | 600/133 |
| 2004/0150319 A1 * | 8/2004 | Tomimatsu et al. | 313/495 |

* cited by examiner

*Primary Examiner*—John Leubecker
*Assistant Examiner*—Philip R Smith
(74) *Attorney, Agent, or Firm*—Blakely, Sokoloff, Taylor & Zafman LLP

(57) ABSTRACT

An autoclavable endoscopic optical coupler includes the capability to optically couple an endoscope and a camera, so that a focused image will be communicated to the camera head. Furthermore, the coupler has the capability of withstanding multiple autoclave sterilization treatments without allowing moisture to penetrate the interior. The coupler includes a lens holder assembly that has an endobody on one portion and a second portion that is inserted into and coupled to a coupler body. The coupler body has a camera attached at one of its ends. A focus ring is physically coupled to the coupler body, which is coupled to the lens holder assembly. Turning the focus ring causes a translation motion of the lens holder assembly and endoscope with respect to the camera head.

1 Claim, 12 Drawing Sheets

AUTOCLAVABLE COUPLER FOR ENDOSCOPIC CAMERA SYSTEM

FIELD OF THE INVENTION

The present invention pertains to the field of medical devices. More particularly, the present invention relates to an optical coupler for endoscopic camera systems.

BACKGROUND OF THE INVENTION

Endoscopy is a medical field which allows the acquisition of high-quality video images of internal features of a human body, without the need for invasive surgery. A basic tool of endoscopy is an endoscopic camera system, which includes a scope that is inserted into the body of a patient. Some endoscopic procedures involve the use of a flexible scope, as in the field of gastroenterology, for example. Other procedures, such as arthroscopy or laproscopy, involve the use of a rigid scope. The scope is normally coupled to a camera head that includes electronics for acquiring video image data through the scope.

The coupled scope and camera head may be held and manipulated during endoscopic surgery by a human surgical assistant or by a holding tool, such as a robotic positioning system. The scope has optical properties which allow it to introduce light into the body of the patient and to transmit light from the body cavity. An optical coupler is generally used to connect the endoscope to the camera head and to transfer the image from the endoscope to the camera head. The camera head is then coupled through a flexible transmission line to a camera control unit, which is often mounted on a mobile cart. The control unit processes video data provided by the camera head to generate images, which are displayed on a video monitor. The control unit may also be coupled to various peripheral devices, such as a printer and a videocassette recorder (VCR).

Although the coupler can have the ability to perform various functions, such as zoom or rotation of the image to change the orientation of the image on the video camera, a coupler typically has the ability to focus the image coming from the endoscope. The focusing function causes the light beams to converge. Focusing is realized when the focal point coincides with a solid-state image sensor, such as a charge coupled device (CCD), incorporated in the camera head. One way of accomplishing this is to install optical components, such as lenses or prisms, within the coupler and attach the camera and scope to the coupler, so that all the components are in optical communication with each other. By moving the optical components relative to either the camera, the scope, or both, the focal distance of the image can thereby be altered, such that focusing is realized.

Because the coupler is used in the medical operating environment, sterilization is necessary before and after each use. Steam autoclaving is a common method of sterilization and is used for many medical instruments that can withstand the necessary high temperature and pressure. The autoclave process can require the instrument to withstand, for example, 135° C. high-pressure vapor for five minutes. Instruments that will not survive the autoclave process are normally sterilized by less efficient techniques, such as immersion in sterilization liquid or gas.

Typically, optical systems are very sensitive to condensation caused by moisture, particularly the moisture in an autoclave environment. Problems that occur with prior art couplers are that moisture from autoclaving is able to penetrate the interior of the optical chamber, causing fogging (condensation) of the lenses and other optical components to occur, which inhibits the coupler's ability to transfer an image from the scope to the camera. A challenge in designing an optical coupler is to prevent moisture from autoclaving and other sources from penetrating the lens system.

One type of endoscope coupler includes a cylindrical body closed at opposite ends by transparent windows and containing a lens holder carrying one or more lenses to optically adjust an endoscopic image onto an image sensor in the camera. The coupler is threaded to accept a camera housing at one portion and an endoscope at the other portion. Focusing is commonly achieved by the user turning a focus ring of the coupler or by operating an electronic control, which translates the lens system inside the coupler. This action varies the distance between the lens and the CCD and allows the image to be focused onto the CCD plane. An illustrative coupler of this type is disclosed in U.S. Pat. No. 6,069,651 (Tsuyuki et al.), which discloses a coupler with a scope attached to one side and a camera attached to the other. As the user turns a focus ring, the lens assembly moves laterally between the camera and scope, which remain at a fixed distance from each other. In this design there is no ability to adjust the focus by altering the distance between the scope and the camera.

The aforementioned U.S. Pat. No. 6,069,651 (Tsuyuki et al.) discloses another endoscopic coupler embodiment where the distance between the scope and lenses is fixed. Turning the camera head, which is provided with threads, can alter the distance between the camera and the fixed scope and lenses. In this design, the camera head provides the ability to alter the distance between the endoscope and the camera. Because the camera head itself facilitates the movement, the camera head must be manufactured with special threads for adjustably coupling the camera head to the coupler body. Furthermore, the camera head must be specially designed to be autoclavable.

SUMMARY OF THE INVENTION

A hermetically sealed optical coupler for an endoscopic camera system includes a coupler body that has a camera attached at one of its ends and partially contains a hermetically sealed lens rider. The lens rider contains at least one lens and has a portion capable of coupling an endoscope. The coupler body is able to cause the endoscope and lens rider to move in unison with respect to the camera.

Other features of the present invention will be apparent from the accompanying drawings and from the detailed description which follows.

BRIEF DESCRIPTION OF THE DRAWINGS

The present invention is illustrated by way of example and not limited in the figures of the accompanying drawings, in which like references indicate similar elements and in which.

DETAILED DESCRIPTION

An autoclavable coupler for endoscopic camera systems is described. As will be described in greater detail below, the coupler includes a body containing one or more focusing lenses, which are hermetically sealed from the outside environment. The body is capable of coupling an endoscope at one side, and a camera head at an opposite side, so that the endoscope and the camera are situated in a path of optical communication with each other and with the lenses located inside the coupler body. The body is constructed so that the distance between the focusing lens or lenses inside the body and the CCD of the camera head can be varied by a simple manipulation of a focus ring. It is through this manipulation that an image being sent from the endoscope is focused onto the CCD, allowing a focused image to be sent from the camera to, and displayed on, a video monitor. The coupler is capable of withstanding repeated autoclave sterilization treatments without moisture penetrating the hermetically sealed optical chamber.

Figure 1:
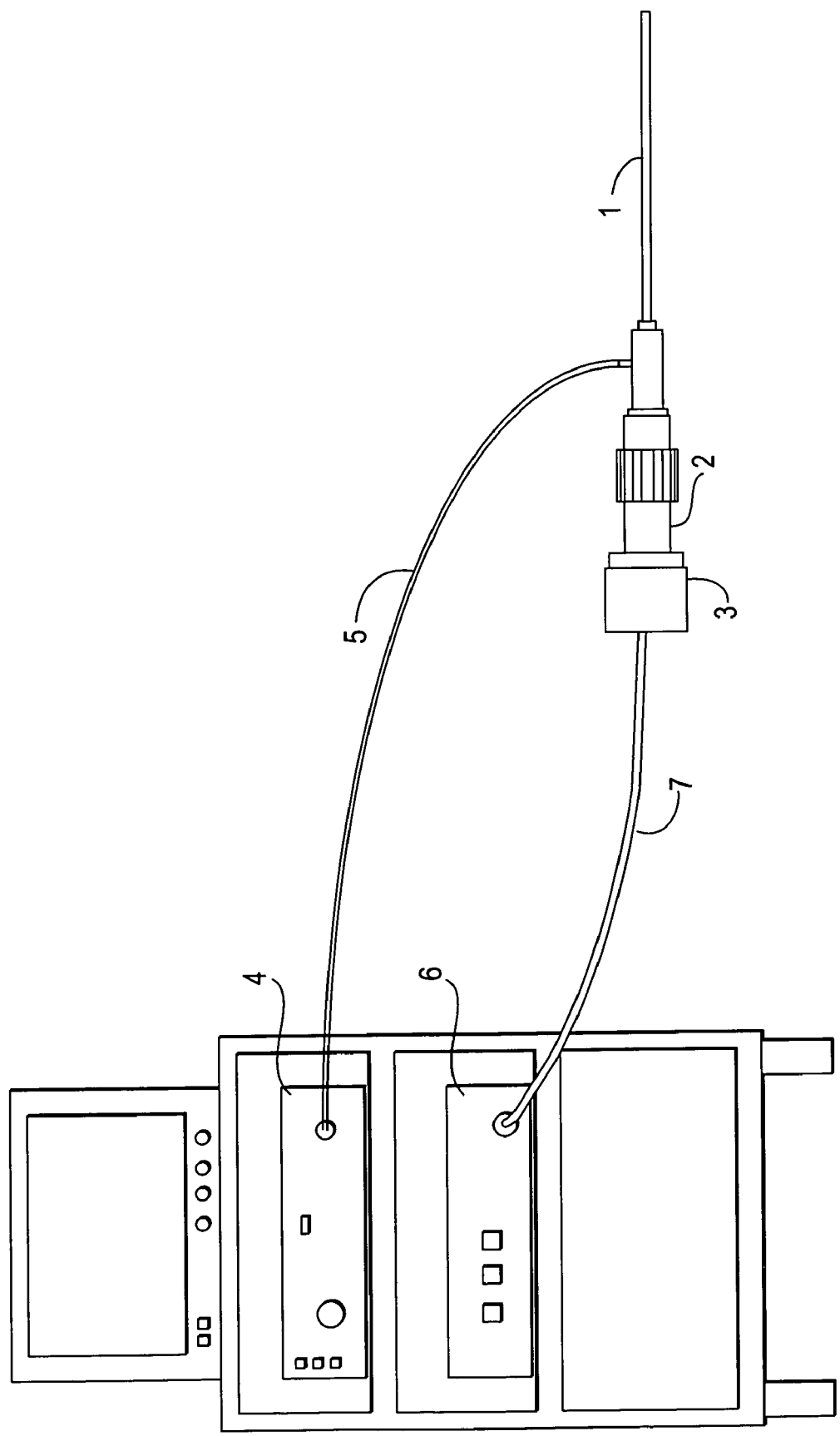
FIG. 1 illustrates an endoscopic camera system.

FIG. 1 illustrates an endoscopic camera system in which a coupler in accordance with the present invention may be used. The illustrated camera system includes a rigid scope 1 of the type that is commonly used for laparoscopy or arthroscopy. The scope 1 is coupled to a camera head 3 by a coupler 2. The camera head 3 includes well-know circuitry, such as CCD's, for acquiring color video image data of internal features of the body through a system of lenses within the scope 1. Light is provided to the scope 1 by a light source 4 through an appropriate flexible light conduit 5, such as a fiber optic cable. The camera head 3 is coupled, and conveys video image data, to a camera control unit (CCU) 6 by a flexible transmission line 7.

Figure 2A:
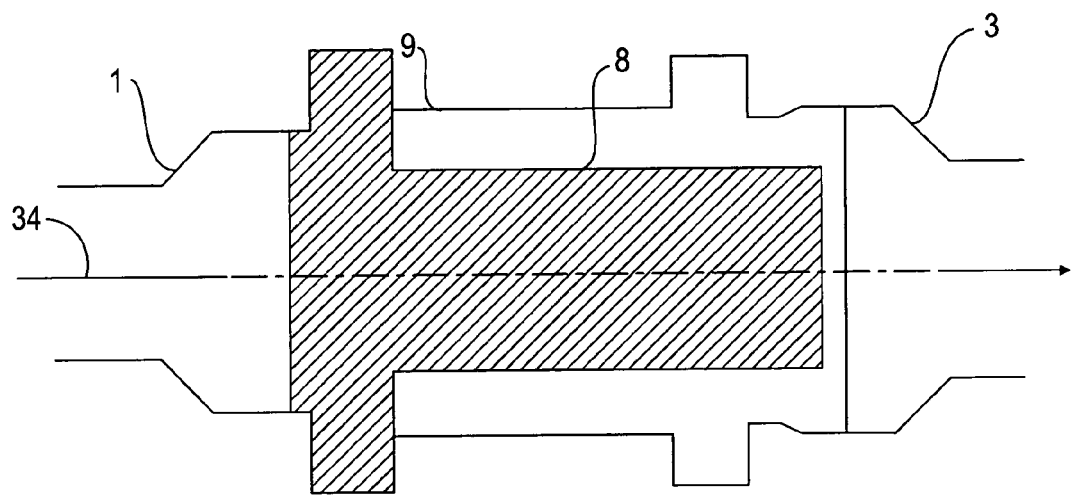
FIG. 2 is a schematic diagram of the endoscopic coupler.

FIG. 2A is a schematic diagram of the endoscopic coupler 2 of FIG. 1, according to one embodiment. The coupler 2 includes a lens holder assembly 8 and a coupler body 9. The lens holder assembly 8 contains at least one lens (not shown). A portion of the lens holder assembly 8 is contained with in the coupler body 9. The portion not contained within the coupler body 9 can be coupled to the endoscope 1. The lens located inside the lens holder assembly 8, as will be explained below, causes an image coming from the endoscope 1 to converge at a focal point some distance away from the endoscope 1. The coupler body 9 can be coupled to the camera head 3. The optical path 34 represents light transmitted from the endoscope 1 through the lens within the lens holder assembly 8 and into the camera head 3.

Figure 2B:
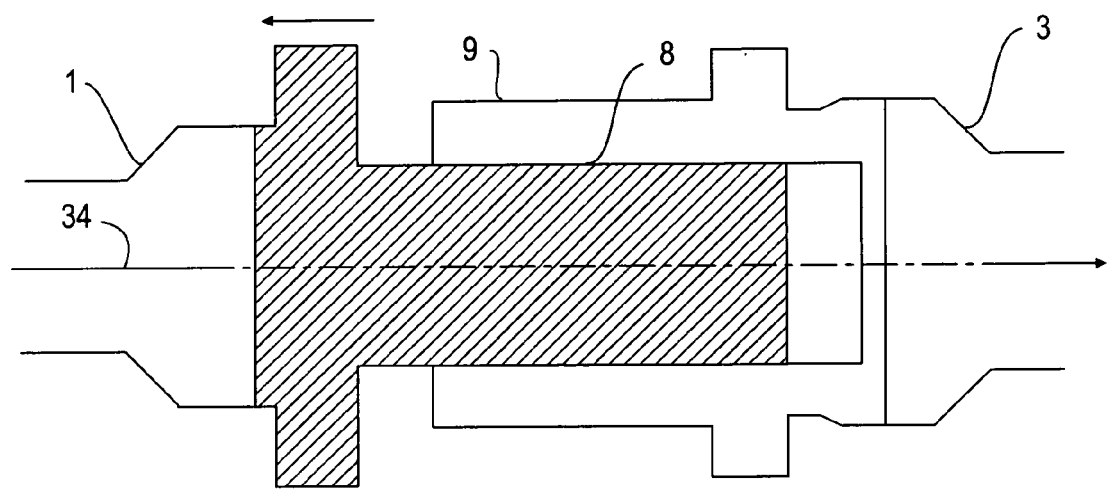

The focusing function is shown in FIG. 2B, where it is shown that the lens holder assembly 8, along with the lens (not shown) and endoscope 1, move in unison parallel to the optical path 34 toward or away from the camera head 3 and the end of coupler body 9. In this way the distance from the camera head 3 to the endoscope 1 and lens combination can be adjusted, so that the focal point falls on the CCD plane of the camera head 3.

Figure 10:
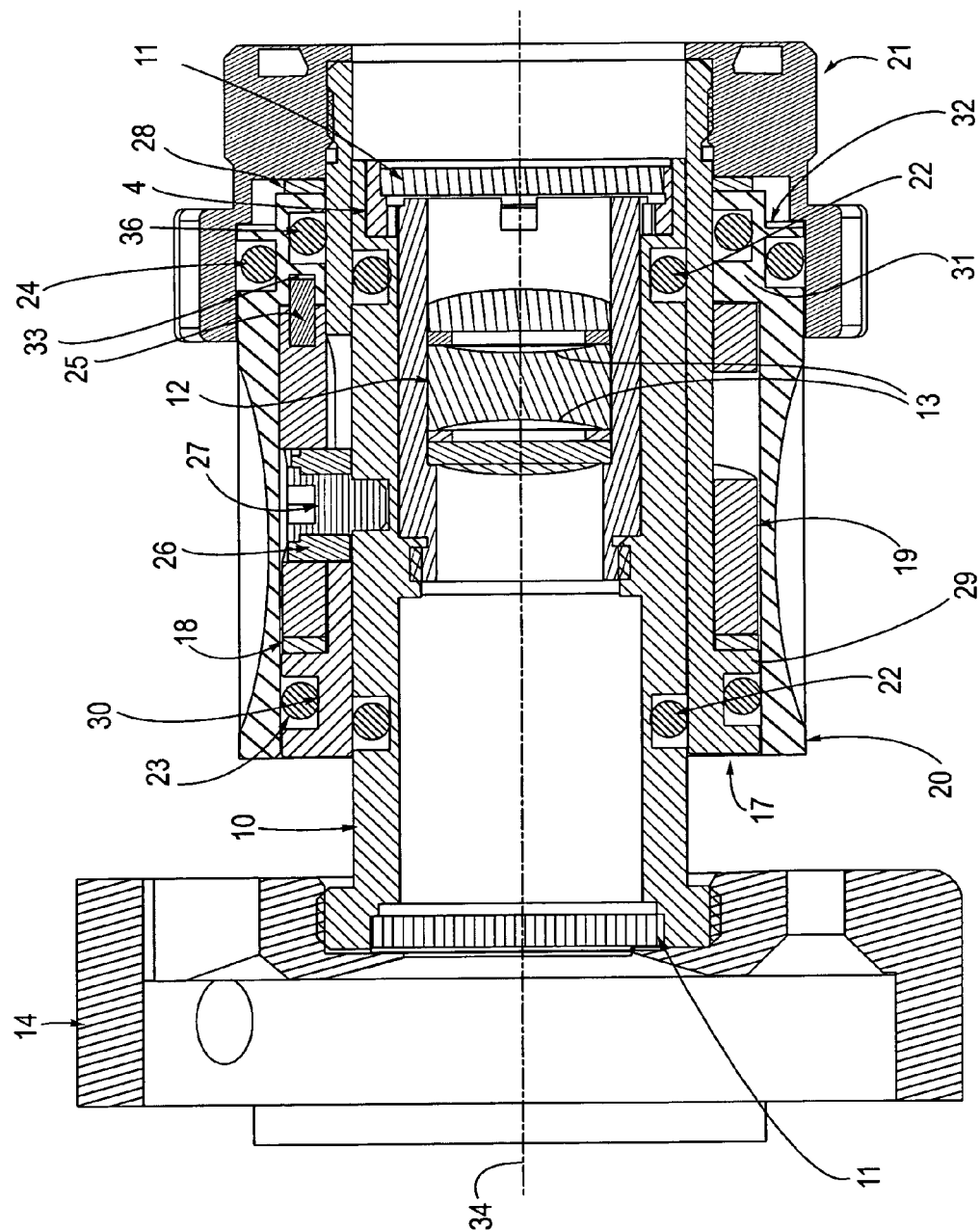
FIG. 10 is a sectional view of an autoclavable coupler for an endoscopic camera system.

FIG. 10 shows a detailed view of one embodiment of the lens holder assembly 8 mated with the coupler body 9. The coupler body 9 comprises a focus tube 17, washers 18 and 28, cam body 19, focus ring 20, press fit pin 25, and camera nut 21. The lens holder assembly 8 comprises a lens rider 10, a window holder 4, a lens holder 12, lenses 13, transparent windows 11, and an endobody 14.

Figure 3:
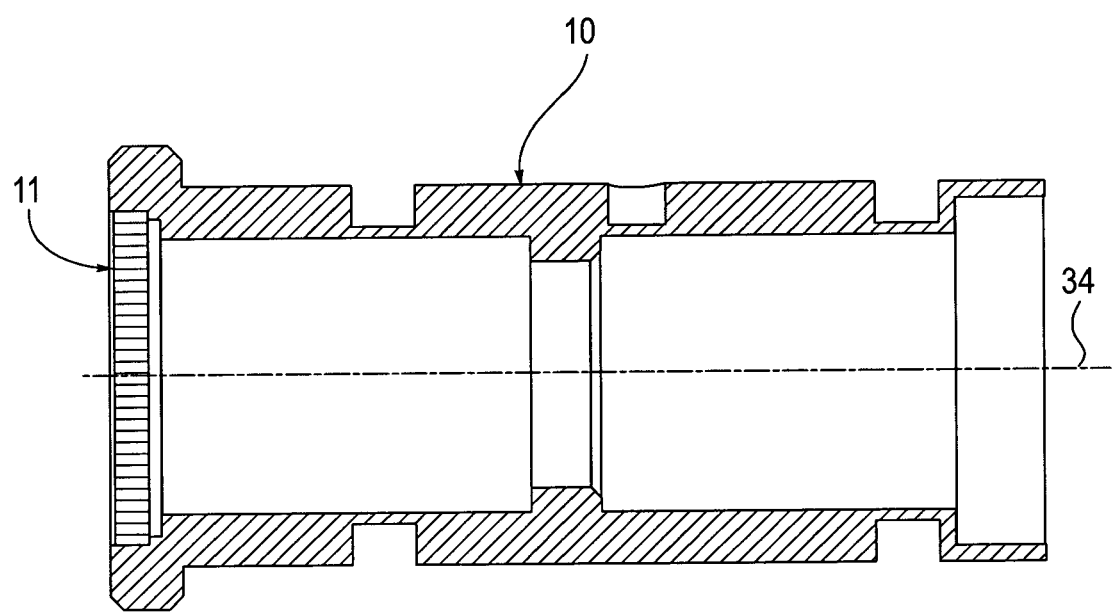
FIG. 3 is a sectional view of a lens rider and transparent cover.

FIG. 3 shows the lens rider 10, which is provided with a transparent cover 11 that is attached to one portion of the lens rider 10. Because the final assembly will be subjected to repeated high pressure and moisture during the autoclaving process the transparent cover 11 is affixed to the lens rider 10 so that the end of the lens rider 10 is watertight. In one embodiment, the transparent cover 11 is made of a crystal glass, such as sapphire, and soldered to the end of the lens rider 10 in a waterproof manner.

Figure 4:
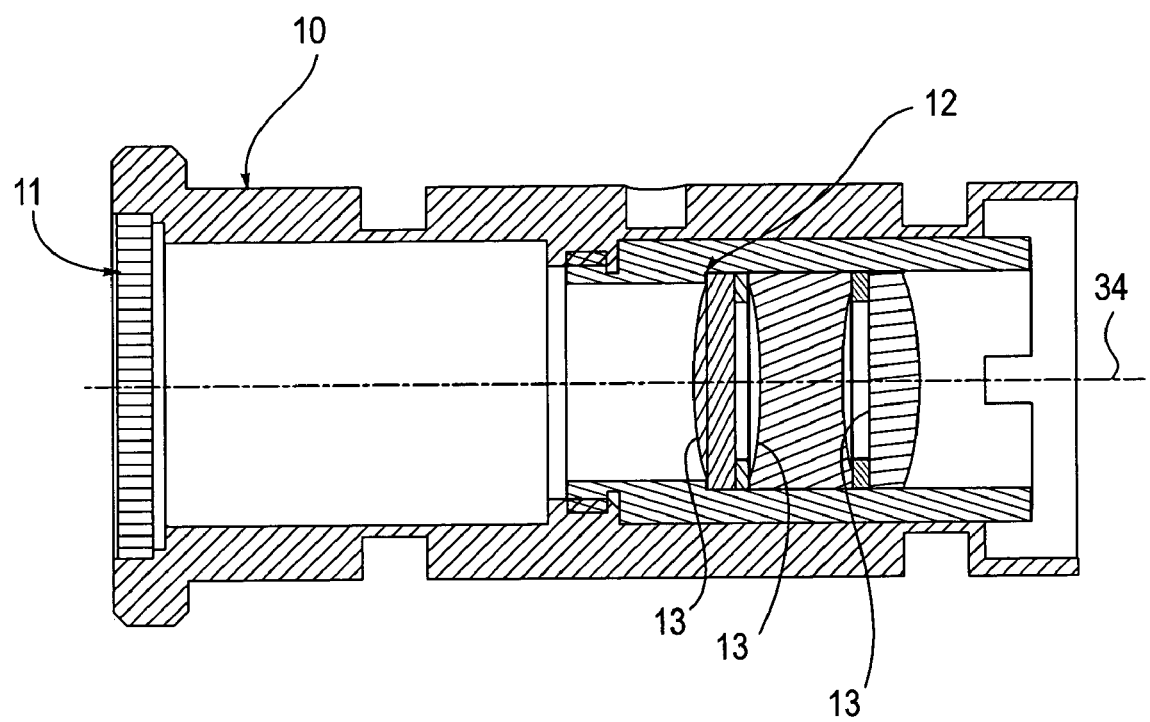
FIG. 4 is a sectional view of the lens rider of FIG. 3 with a lens holder inserted into the lens rider.

FIG. 4 shows the lens holder 12 inserted into the lens rider 10. In the embodiment shown, the lens holder 12 contains three focusing lenses 13. It should be noted that any alternative type of lens system could be used. The lenses 13 can vary in characteristics such as shape, size, thickness, type, etc, depending on the application. In one embodiment, the lens holder 12 and lens rider 10 are provided with mating threads so that lens holder 12 can be screwed into lens rider 10 to affix the lenses 13 in the optical path. Other methods of coupling the lens holder 12 to the interior of the lens rider 10 may also be used.

Figure 5:
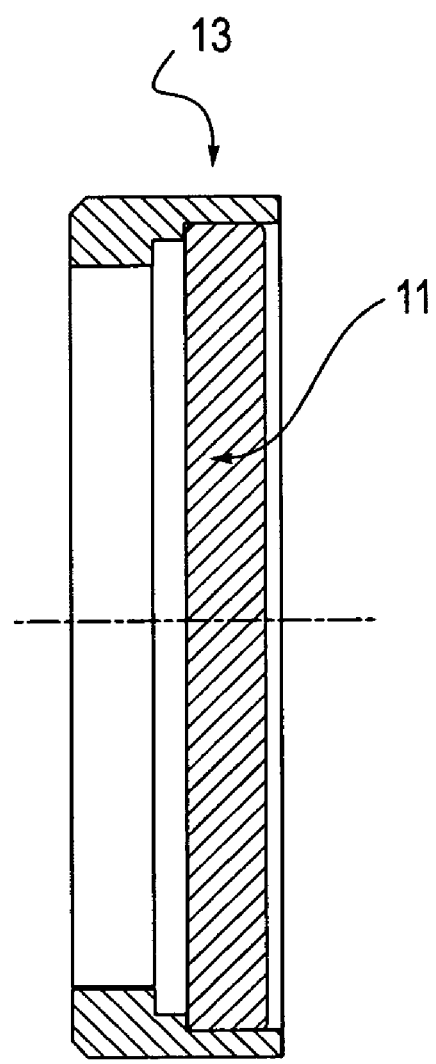
FIG. 5 is a sectional view of a window holder and transparent cover.

FIG. 5 shows the window holder 13 fitted with a transparent cover 11. Cover 11 is constructed and attached to the window holder 13 to create a watertight seal between the window holder 13 and the transparent cover 11. Any material that will easily allow light to pass, while preventing the intrusion of moisture, may be used as the transparent cover 11. In order to acquire heat resistance to autoclaving however, it is desirable that the transparent cover 11 is constructed not with a common optical member, but of crystal glass, like sapphire, quartz, or rock crystal. In one embodiment, the transparent cover 11 is soldered to the end of the window holder 13 in a waterproof manner.

Figure 6:
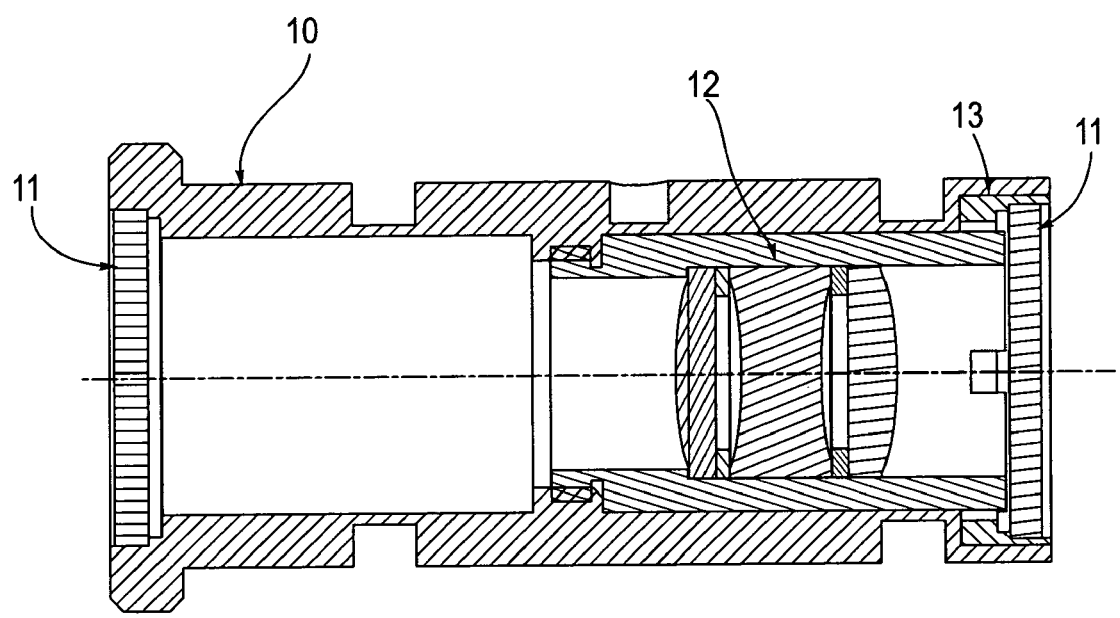
FIG. 6 is a sectional view of the lens rider shown in FIG. 4 with the window holder of FIG. 5 attached.

In FIG. 6, the window holder 13 is shown attached to the lens rider 10. In one embodiment, laser welding is used to attach the window holder 13 to the lens rider 10. Laser welding is suitable for precise and fine processes, because it provides deep fusion and little thermal distortion. In one embodiment, the welding process is performed in a chamber filled with a condensation-inhibiting gas, such as Helium or Nitrogen, for example. The effect of the laser welding is to create a hermetically sealed environment inside of the lens holder assembly 8. If the laser welding is performed in a chamber filled with only a condensation-inhibiting gas, only that gas will be present inside of the hermetically sealed lens holder assembly 8. Therefore, the amount of moisture inside the assembly 8 will be minimal at the time of manufacture, and condensation will be inhibited.

Figure 7:
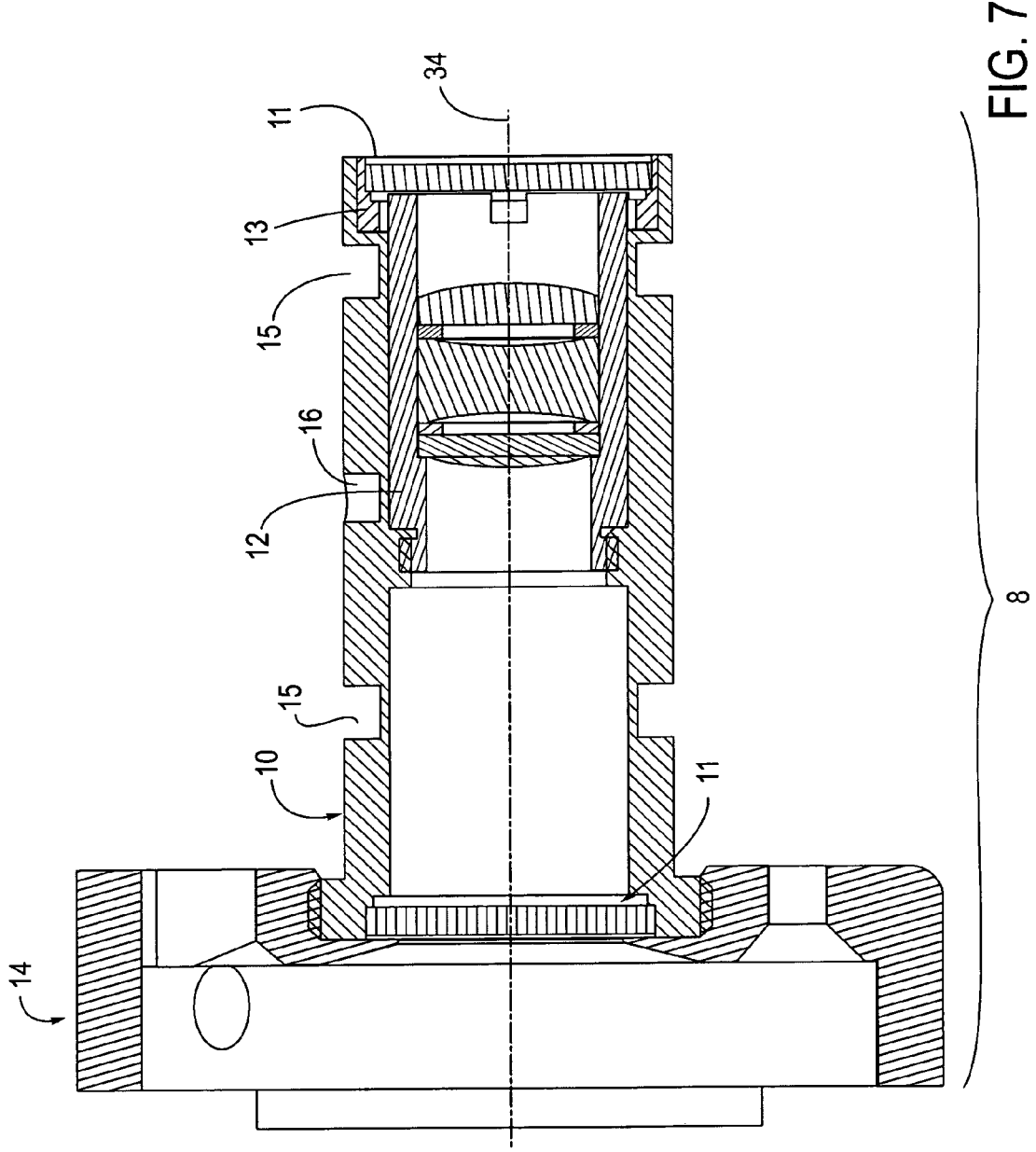
FIG. 7 is a sectional view of the hermetically sealed lens holder assembly.

As shown in FIG. 7, the lens rider 10 is removably coupled to the endobody 14 for attaching the endoscope 1 to the lens rider 10. In one embodiment, the lens rider 10 is provided with threads on its outside surface at the portion opposite the window holder 13. The endobody 14 is also provided with threads on an inside surface, which are constructed as to have the ability to mate with the threads of the lens rider 10. Attaching endobody 14 to the lens rider 10, as shown in FIG. 7, completes the assembly of lens holder assembly 8.

Figure 8:
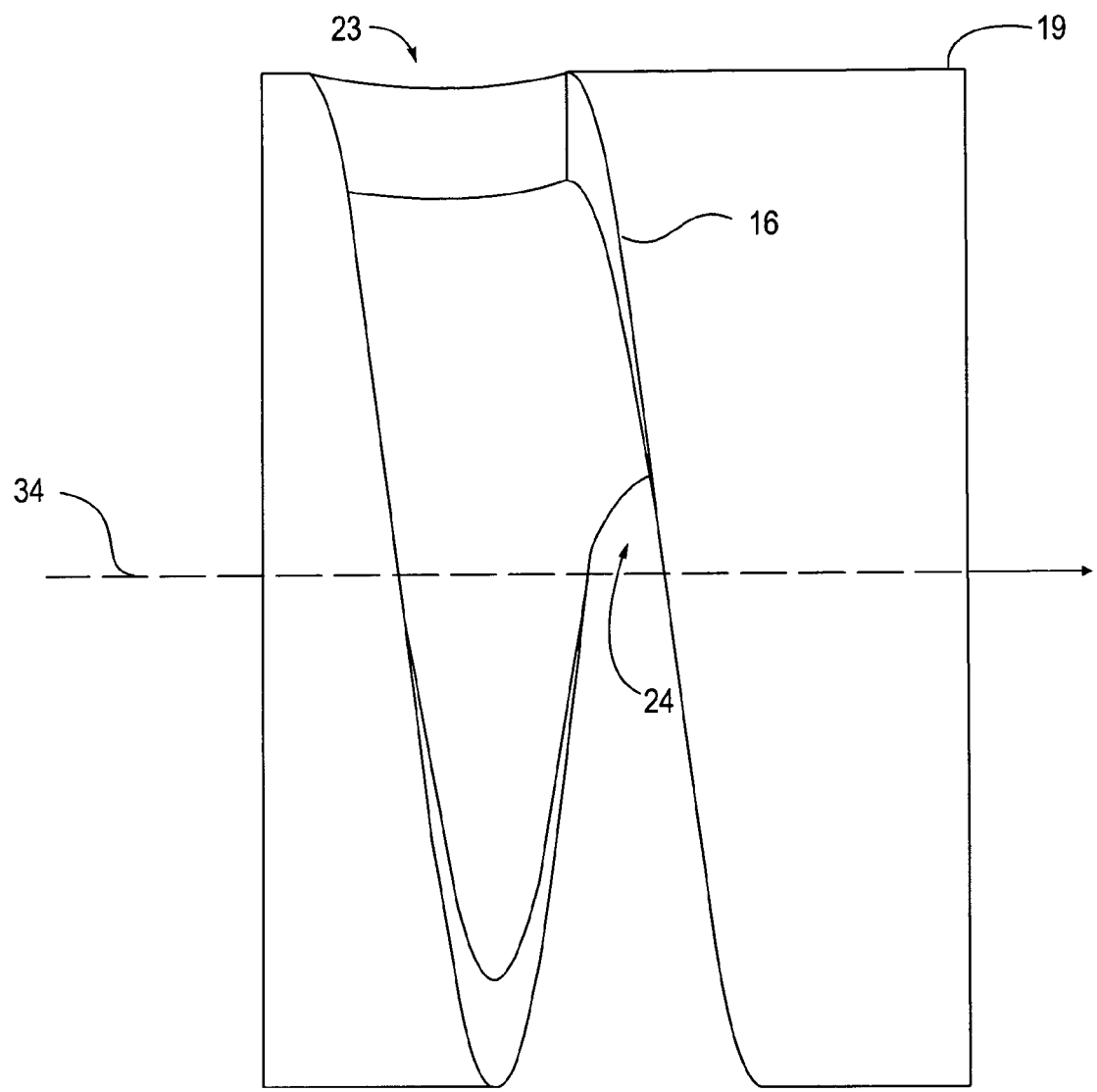
FIG. 8 illustrates the cam body with helical groove.
Figure 9:
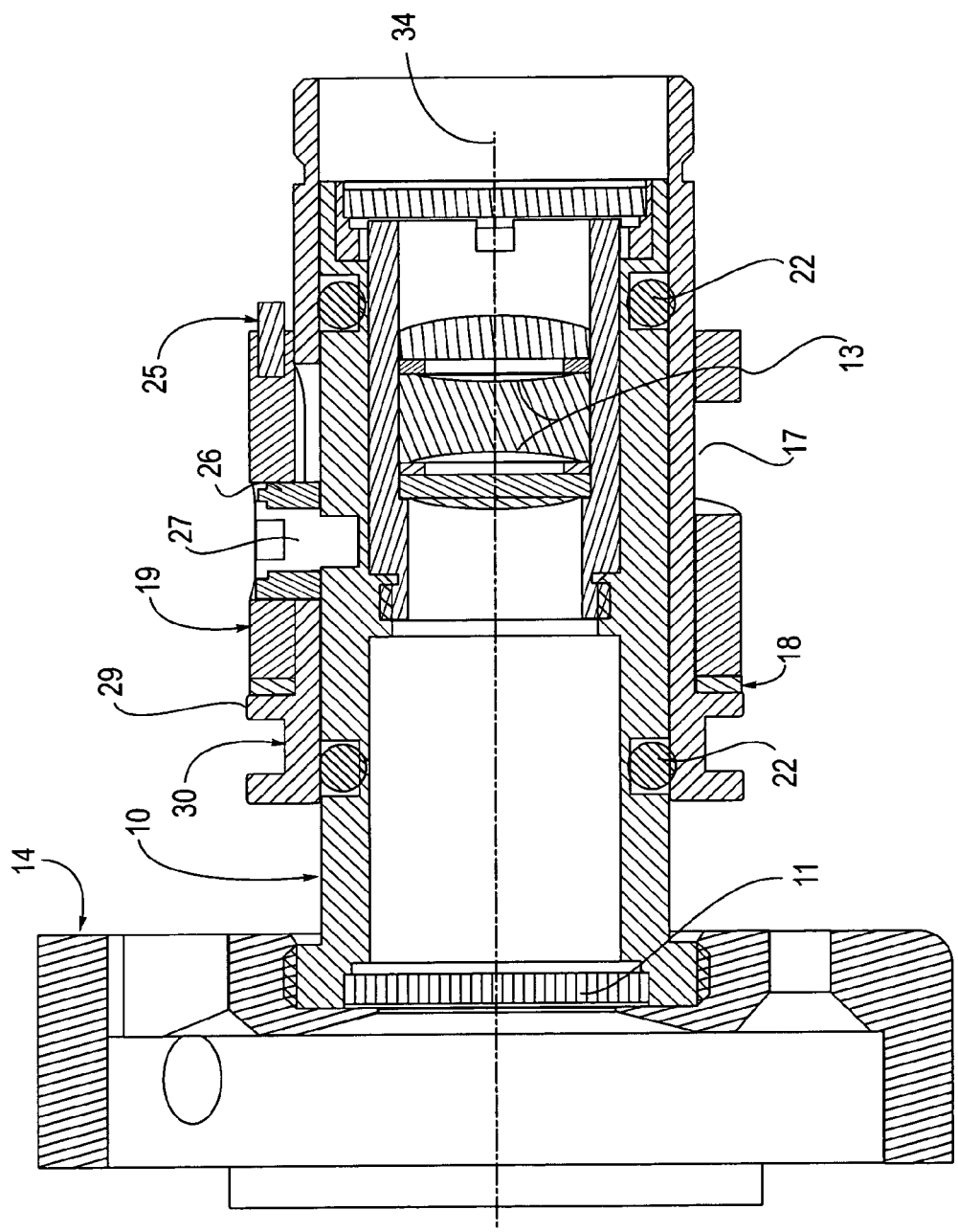
FIG. 9 is a sectional view of the lens holder assembly and endobody shown in FIG. 7 physically coupled to a focus tube and cam body.

In the illustrated embodiment, the lens rider 10 is cylindrical. The lens rider 10 is provided with two continuous ring grooves 15 disposed within its outside surface. The ring grooves 15 are provided to hold O-rings 22, as shown in FIG. 9. There is also a groove 16 in the cam body 19, as shown. The groove 16 can also be seen in FIG. 8. End 24 of groove 16 is closer to the window holder 4 than is end 23 of the groove 16. It can be seen that the groove 16 is helical in shape, with the optical path 34 as its center axis. In other embodiments, the lens rider 10 may not be cylindrical, in which cases the groove 16 may not be helical.

In FIG. 9, the lens holder assembly 8 is shown inserted into and coupled to the focus tube 17 and the cam body 19. In this embodiment, O-rings 22 are placed into the ring grooves 15 on the lens rider 10. The lens rider 10 and O-rings 22 are then placed inside the focus tube 17. The inside diameter of the focus tube 17 is of a dimension close enough to the outside diameter of the lens rider 10 so that the O-rings 22 are compressed. The focus tube 17 has a flange 29 at the end containing the lens rider 10, with the opposite end of the focus tube 17 being provided with threads for coupling to a camera mount 21 (not shown). The focus tube flange 29 has a groove 30 that runs along the outer surface of the flange 29.

FIG. 10 shows the final assembly of the optical coupler 2. As can be seen in FIG. 10, an O-ring 23 is placed into the groove 30 so that when the focus ring 20 is later placed over the focus tube 17, the O-ring 23 will compress and further seal the components of the coupler body 9 and lens holder assembly 8. A washer 18 is place onto the focus tube 17 and butted against the flange 29. A cam body 19 is then placed over the focus tube 17 so that the washer 18 is between the cam body 19 and the flange 29 of the focus tube 17. Washer 18 is preferably manufactured from a material capable of reducing friction between the focus tube 17 and cam body 19.

The coupler body 9 and the lens holder assembly 8 (see FIGS. 2A and 2B) are coupled together by a screw 27. Referring still to FIG. 10, a roller 26 is fitted into, and constrained by, the helical groove 16 in the cam body 19. The roller 26 is slidably fitted against screw 27, such that the head of screw 27 sits inside the roller 26. The focus tube 17 and lens holder assembly 8 are aligned, such that the screw 27 extends through the roller 26 and focus tube 17 to screw into a threaded recess in the lens rider 10.

A pin 25 couples the cam body 19 to the focus ring 20. Focus ring 20 has a flange 31 on its inside surface and constrains the cam body 19 onto the focus tube 17. Similarly to the flange 29 with groove 30 of the focus tube 17, the focus ring flange 31 has a groove 32. The groove 32 is fitted with an O-ring 36 which, when the coupler body 9 is assembled, makes constant sealing contact with focus tube 17. The flange 31 is also provided with a recess 33. Recess 33 is designed to accept a portion of press fit pin 25, thereby coupling the cam body 19 and the focus ring 20.

When the focus ring 20 is rotated about the optical axis 34, the cam body 19 is also rotated as a result of its being coupled by pin 25 to the focus ring 20. The rotation of the cam body 19, due to the helical groove 16 in the cam body 19 (see FIG. 8), causes the roller 26 and screw 27 to translate together parallel to the optical axis 34. Since the lens rider 10 is attached to the screw 27, the lens rider 10 also translates parallel to the optical axis 34. Note that, in other embodiments, other techniques can be used to cause translation parallel to the optical axis 34 such as described above.

The camera nut 21, shown in FIG. 10, is provided with threads on its inside surface so that the camera nut 21 can be screwed onto threads provided on the outside surface of focus tube 17. As shown in FIG. 10, washer 28 is inserted onto focus tube 17 and camera nut 21 is screwed onto the focus tube 17, thereby preventing focus ring 20 from separating from the cam body 19 and press fit pin 25. The camera nut 21 is also capable of coupling a camera head 3 to the coupler body 9. When the camera head 3 is attached to the camera nut 21, a turning motion of the focus ring 20 causes the distance from the camera head 3 to the endoscope 1 and the lens holder assembly 8 to vary, thereby allowing the focus function to occur.

Figure 11A:
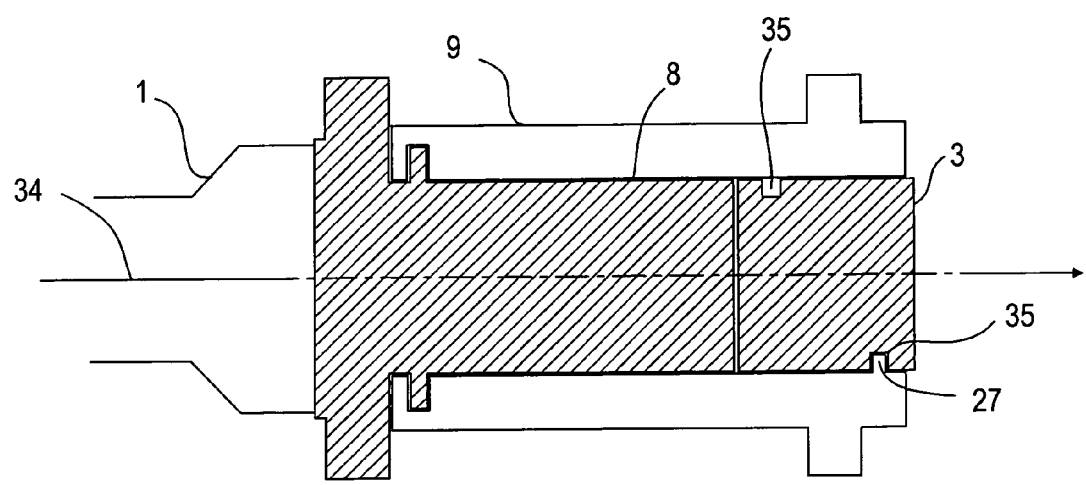
FIG. 11 shows an alternate embodiment for the autoclavable coupler for the endoscopic camera system shown in FIG. 10.
Figure 11B:
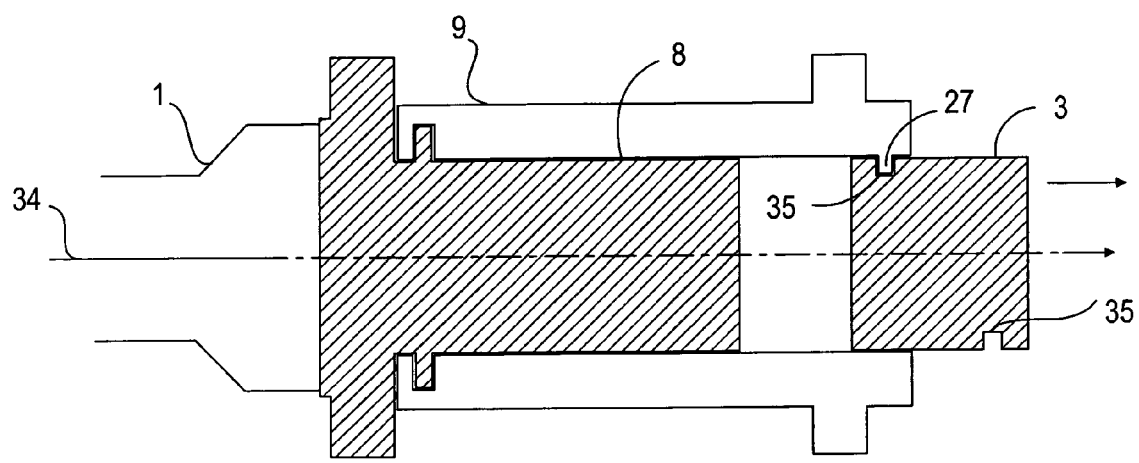

Another embodiment of the invention is shown in FIGS. 11A and 11B. In the embodiment shown in FIG. 11A, the lens holder assembly 8 is contained by the coupler body 9. Lens holder assembly 8 contains at least one focus lens (not shown). Coupler body 9 is designed so that the body 9 can rotate around the lens holder assembly 8 with the lens holder assembly 8 and coupler body 9 remaining at a stationary distance relative to each other. Camera head 3 is provided with a helical groove 35. Coupler body 9 is also provided with a member 27 that penetrates groove 35. As can be seen in FIG. 11B, as coupler body 9 is rotated, the member 27 follows the helical groove 35 and causes a translation motion of the camera head 3 with respect to the endoscope 1 and lens holder assembly 8. This allows the CCD plane of the camera head 3 to be moved until it coincides with the focal point of the lenses.

Figure 12:
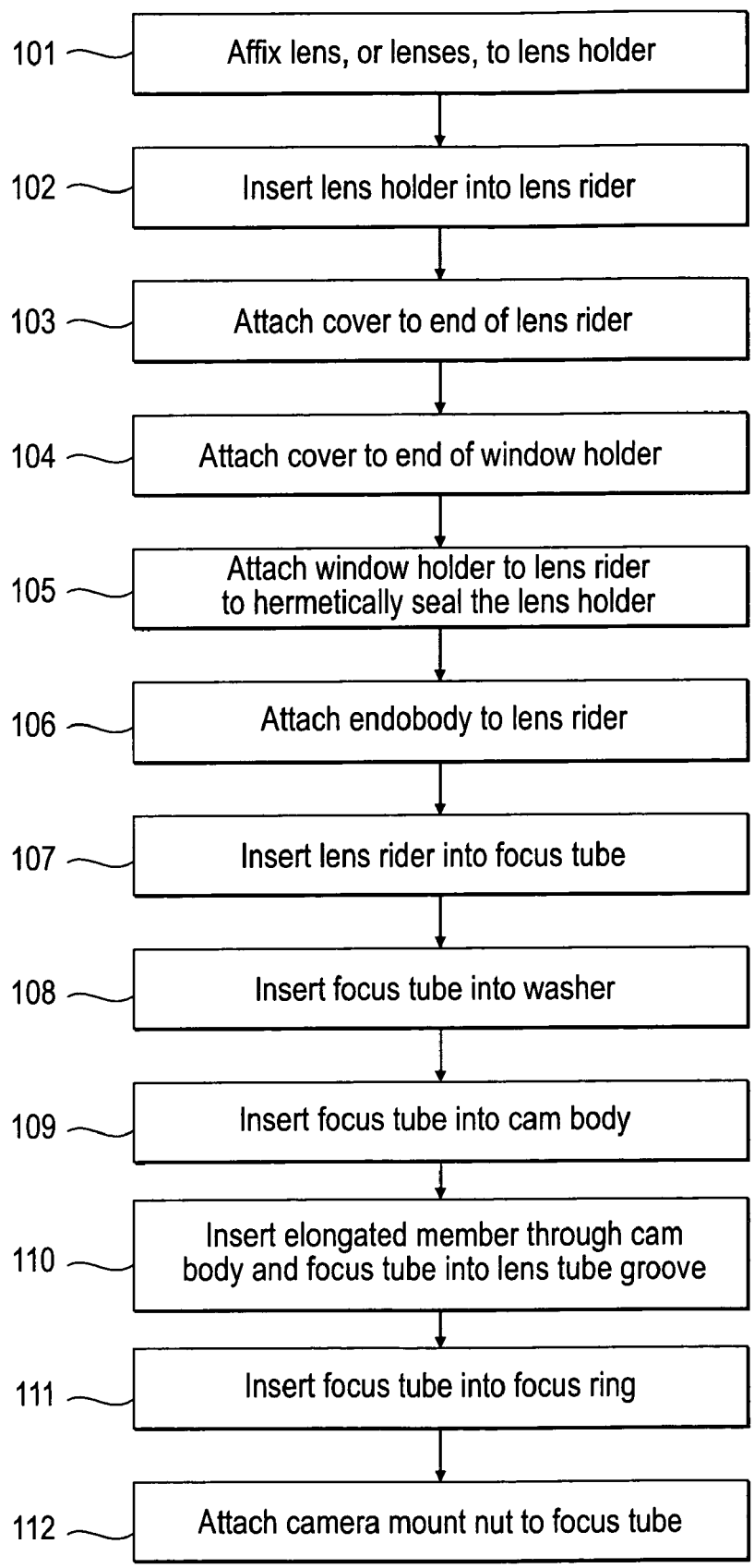
FIG. 12 is a flow chart of a process for manufacturing the autoclavable coupler for an endoscopic camera system.

FIG. 12 is a flow chart describing a process of manufacturing the autoclavable coupler 2. The process is described in boxes 101 through 112. As can be seen from box 101, the process begins with affixing a lens, or lenses, 13, to the lens holder 12. Next, as seen in box 102, the lens holder 12 is inserted into the lens rider 10. Box 103 then describes that cover 11 is attached to the lens rider 10. Box 104 details that a second cover 11 is attached to the window holder 13. As described in box 105, the window holder 13 is attached to the lens rider 10 to hermetically seal the lens holder 12 inside. Then, an endobody 14 is attached to the lens rider 10, as stated in box 106, and the lens rider 10 is inserted into the focus tube 17, as detailed in box 107. Box 108 describes that the focus tube 17 is inserted into the washer 18. Box 109 describes that the focus tube 17 is also inserted into the cam body 19. At this point, as described in box 110, an elongated member 27 is inserted through the cam body 19 and the focus tube 17 and into the groove 16 in the lens rider 10. As stated in box 111, the focus tube 17 is inserted into the focus ring 20 and a second washer 28. Lastly, box 112 describes that the camera nut 21 is attached to the focus tube 17.

Thus, an autoclavable coupler for an endoscopic camera system has been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative sense rather than a restrictive sense.

What is claimed is:

1. An optical coupler comprising:
   a lens holder containing a plurality of lenses disposed along an optical axis;
   a lens rider containing the lens holder, the lens rider having a first end and a second end;
   a transparent cover attached to the first end of the lens rider to seal the first end from moisture intrusion;
   a window holder having a first portion and a second portion, the first portion of the window holder having a transparent cover sealing the first portion from moisture intrusion, the second portion of the window holder attached to the first end of the lens rider so as to hermetically seal the interior of the lens rider;

a condensation-inhibiting gas inside the hermetically sealed lens rider;

an endobody, at which an endoscope can be coupled to the lens rider, attached to the first end of the lens rider;

a focus tube containing at least a portion of the lens rider;

a cam body disposed about the focus tube, the cam body having a helical groove disposed therein;

a roller disposed within the helical groove in the cam body;

a member disposed through a hole in the roller and having a first portion attached to the focus tube and a second portion attached to the lens rider;

a focus ring surrounding the cam body to turn the cam body and the focus tube about an optical axis of the optical coupler; and a camera-mount nut attached to the focus tube to constrain the focus ring on the cam body and capable of coupling a camera to the focus tube.

* * * * *